US00PP19895P2

(12) United States Plant Patent
Uchneat

(10) Patent No.: US PP19,895 P2
(45) Date of Patent: Apr. 7, 2009

(54) *IMPATIENS* PLANT NAMED 'BALOLESPRI'

(50) Latin Name: *Impatiens walleriana*
Varietal Denomination: Balolespri

(75) Inventor: Michael S. Uchneat, Bellefonte, PA (US)

(73) Assignee: Ball Horticultural Company, West Chicago, IL (US)

( * ) Notice: Subject to any disclaimer, the term of this patent is extended or adjusted under 35 U.S.C. 154(b) by 29 days.

(21) Appl. No.: 11/823,202

(22) Filed: Jun. 27, 2007

(51) Int. Cl.
*A01H 5/00* (2006.01)

(52) U.S. Cl. ..... Plt./317

(58) Field of Classification Search ..... Plt./317
See application file for complete search history.

(56) References Cited

PUBLICATIONS

UPOV ROM GTITM Computer Database, GTI Jouve Retreival Software Feb. 2008 Citations For 'Balolespri'.*

* cited by examiner

*Primary Examiner*—Wendy C. Haas
(74) *Attorney, Agent, or Firm*—Audrey Charles

(57) ABSTRACT

A new and distinct cultivar of *Impatiens* plant named 'Balolespri', characterized by its double type, dark purple and white bicolored flowers, medium green-colored foliage, and moderately vigorous, mounded growth habit.

1 Drawing Sheet

Latin name of genus and species of plant claimed: *Impatiens walleriana.*
Variety denomination: 'Balolespri'.

BACKGROUND OF THE INVENTION

The present invention relates to a new and distinct cultivar of *Impatiens* plant botanically known as *Impatiens walleriana* and hereinafter referred to by the cultivar name 'Balolespri'.

The new cultivar originated in a controlled breeding program in Elburn, Ill. during July 2002. The objective of the breeding program was the development of *Impatiens* cultivars with fully double-type flowers, attractive flower and foliage coloration, and a freely branching, compact growth habit.

The new *Impatiens* cultivar was the result of a self-pollination of the proprietary *Impatiens walleriana* breeding selection designated 3684-2, not patented, characterized by its single type violet rose-colored flowers, medium green-colored foliage, and mounded growth habit. The new cultivar was discovered and selected as a single flowering plant within the progeny of the above stated self-pollination during January 2003 in a controlled environment at Elburn, Ill.

Asexual reproduction of the new cultivar by terminal stem cuttings since January 2003 at Elburn, Ill. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balolespri' as a new and distinct cultivar of *Impatiens* plant:

1. Double type, dark purple and white bicolored flowers;
2. Medium green-colored foliage; and
3. Moderately vigorous, mounded growth habit.

Plants of the new cultivar differ from plants of the parent primarily in flower form and flower color.

Of the many commercially available *Impatiens* cultivars known to the inventor, the most similar in comparison to the new cultivar is SILHOUETTE Rose Star 'Silte Ros07' U.S. Plant Pat. No. 19,139. However, in side by side comparisons, plants of the new cultivar differ from plants of 'Silte Ros07' in the following characteristics:

1. Plants of the new cultivar have larger flowers, as measured by flower width and depth, than plants of 'Silte Ros07'; and
2. Plants of the new cultivar have a flower color different from plants of 'Silte Ros07'.

Of the many commercially available *Impatiens* cultivars known to the inventor, another cultivar similar in comparison to the new cultivar is SILHOUETTE Purple 'Silte Pur', not patented. However, in side by side comparisons, plants of the new cultivar have a flower color different from plants of 'Silte Pur'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balolespri'. The plants were grown in 4.5 inch pots for 6 weeks in a greenhouse at West Chicago, Ill. Plants were given one pinch at transplant.

DETAILED BOTANICAL DESCRIPTION

Figure 1:
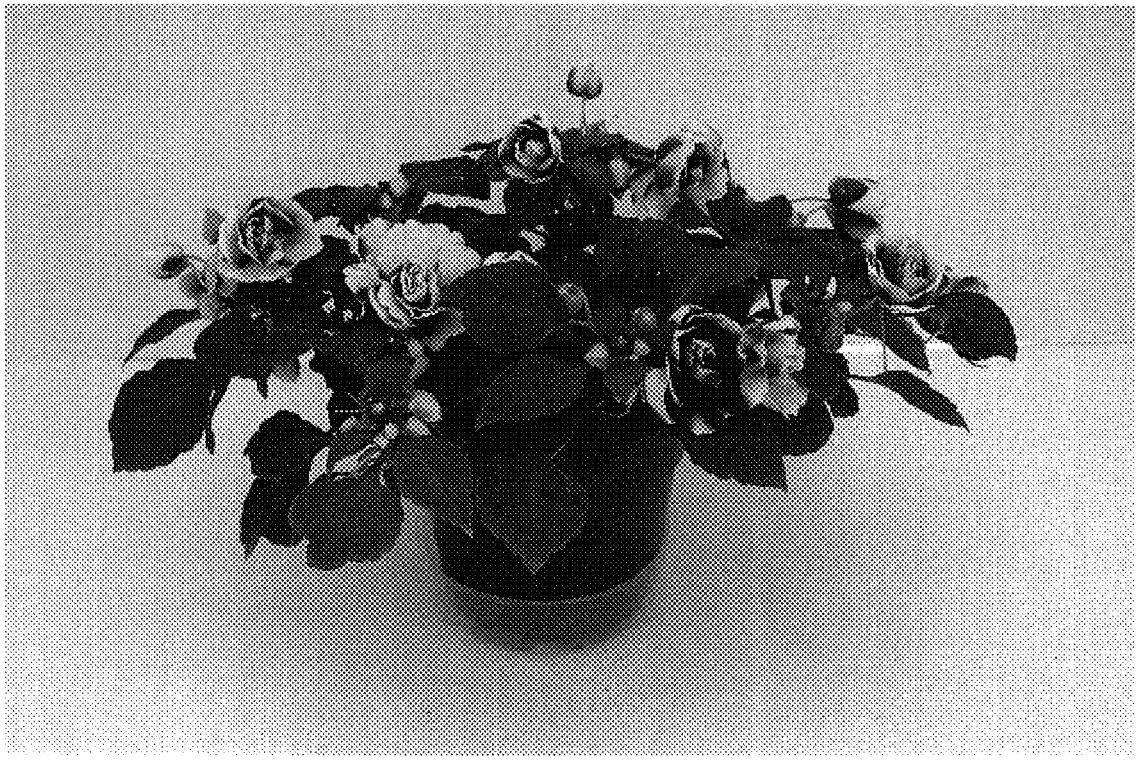
FIG. 1 illustrates a side view of the overall growth and flowering habit of 'Balolespri'.
Figure 2:
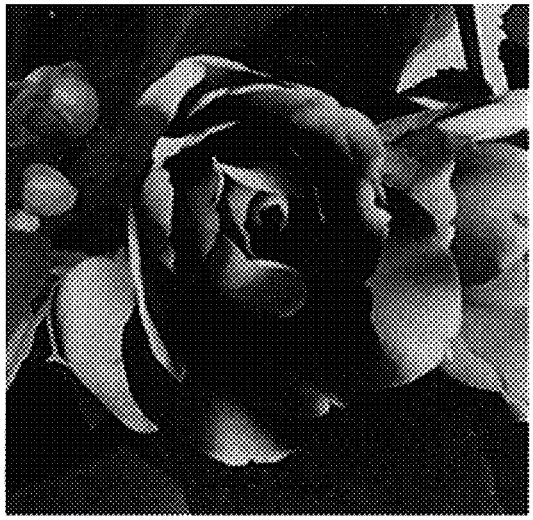
FIG. 2 illustrates a close-up view of an individual flower of 'Balolespri'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on May 2, 2007 between 1:00 p.m. and 3:00 p.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 6 weeks utilizing a soilless growth medium. Plants were given one pinch at transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Impatiens walleriana* cultivar Balolespri.

Parentage:

*Parent.*—Proprietary *Impatiens walleriana* breeding selection designated 3684-2, not patented.

Propagation:

*Type cutting.*—Terminal stem.

*Time to initiate roots.*—Approximately 7 to 8 days.

*Time to produce a rooted cutting.*—Approximately 21 to 24 days.

*Root description.*—Fibrous.

*Rooting habit.*—Freely branching.

Plant description:

*Commercial crop time.*—Approximately 5 to 7 weeks from a rooted cutting to finish in a 10 cm pot.

*Growth habit and general appearance.*—Moderately vigorous, mounded growth habit.

*Size.*—Height from soil level to top of plant plane: Approximately 12.8 cm. Width. Approximately 26.9 cm.

*Branching habit.*—Freely branching, pinching improves basal branching. Quantity of main branches per plant: Approximately 5.

*Branch.*—Strength: Moderately strong. Length: Approximately 11.7 cm. Diameter at central internode: Approximately 4.1 mm. Length of central internode: Approximately 2.1 cm. Texture: Glabrous. Color of young stem: 143D with streaks of 187B. Color of mature stem: 143C with streaks of 187B. Streaks are wider at the node regions.

Foliage description:

*General description.*—Quantity of leaves per main branch: Approximately 9. Fragrance: None. Form: Simple. Arrangement: Alternate.

*Leaves.*—Aspect: Acute angle to stem, becoming perpendicular with age. Shape: Ovate. Margin: Crenate, ciliate. Apex: Acute. Base: Attenuate. Venation pattern: Pinnate. Length of mature leaf at center of stem: Approximately 4.8 cm. Width of mature leaf at center of stem: Approximately 3.3 cm. Texture of upper surface: Sparsely pubescent. Texture of lower surface: Glabrous. Color of upper surface of young foliage: 137A with venation of 137B. Color of lower surface of young foliage: N187A with splotches of 191B and venation of 191C. Color of upper surface of mature foliage: Darker than 137A with venation of darker than 137B. Color of lower surface of mature foliage: N187B with splotches of 191B and venation of 191C.

*Petiole.*—Length: Approximately 2.0 cm. Diameter: Approximately 2.0 mm. Texture: Glabrous. Color: 138B with streaks of 187B.

Flowering Description:

*Flowering habit.*—'Balolespri' is freely flowering under outdoor growing conditions with substantially continuous blooming from spring through autumn and year-round in greenhouse environment.

*Lastingness of individual flower on the plant.*—Approximately 6 to 7 days.

Flower description:

*General description.*—Type: Double. Quantity per plant: Approximately 9. Fragrance: None.

*Bud.*—Rate of opening: Generally takes 2 to 3 days for bud to progress from first color to fully open flower. Quantity showing color per plant: Approximately 11.

*Bud just before opening.*—Shape: Ovoid. Length: Approximately 1.8 cm. Diameter: Approximately 1.2 cm. Color: N78B.

*Corolla.*—Shape: Hemispherical. Width: Approximately 4.0 cm. Depth: Approximately 2.1 cm. Borne: Above and below foliage.

*Petals.*—Quantity: 25. Shape: Obovate; innermost are irregular. Aspect: Flat. Appearance: Iridescent. Margin: Entire. Apex: Obtuse; some are emarginate. Base: Attenuate. Length of outermost petal: Approximately 2.6 cm. Width of outermost petal: Approximately 2.1 cm. Length of innermost petals: Approximately 1.2 cm. Width of innermost petals: Approximately 9.1 mm. Texture of upper and lower surfaces: Glabrous. Color of upper surface when first open: Irregular striping of N78A and purer white than 155D. Color of lower surface when first open: Irregular striping of between N78A and N78B and purer white than 155D. Color of upper surface when fully open: Irregular striping of N79C and purer white than 155D. Color of lower surface when fully open: Irregular striping of N78B and purer white than 155D.

*Spur.*—Quantity: 1 per flower. Length: Approximately 3.7 cm. Diameter at tip: Less than 1 mm. Diameter at base: Approximately 2.0 mm. Texture: Glabrous. Color: 145B with tip of 185B.

*Peduncle.*—Strength: Moderately strong. Aspect: Acute angle to stem. Length: Approximately 3.6 cm. Diameter: Approximately 2.0 mm. Texture: Glabrous. Color: 144B.

*Sepals.*—Quantity per flower: 4 with one fused to base of upper petal. Shape of lateral sepals: Lanceolate. Shape of lower sepal: Ovate. Apex of all sepals: Acute. Length of lateral sepals: Approximately 3.0 mm. Width of lateral sepals: Approximately 1.0 mm. Length of lower sepal: Approximately 1.2 cm. Width of lower sepal: Approximately 9.0 mm. Texture of upper and lower surfaces of all sepals: Glabrous. Color of lateral sepals: 144A. Color of lower sepal: 145D with tip of 144A.

*Reproductive organs.*—None observed.

Seed and fruit production: Neither seed nor fruit production has been observed.

Disease and pest resistance: Resistance to pathogens and pests common to *Impatiens* has not been observed.

What is claimed is:

1. A new and distinct cultivar of *Impatiens* plant named 'Balolespri', substantially as herein shown and described.

* * * * *